(12) United States Patent
Nagayama

(10) Patent No.: US 11,534,380 B2
(45) Date of Patent: Dec. 27, 2022

(54) HAIR TREATMENT METHOD

(71) Applicant: KAO CORPORATION, Tokyo (JP)

(72) Inventor: Ayami Nagayama, Mizuho (JP)

(73) Assignee: KAO CORPORATION, Tokyo (JP)

( * ) Notice: Subject to any disclaimer, the term of this patent is extended or adjusted under 35 U.S.C. 154(b) by 91 days.

(21) Appl. No.: 16/765,046

(22) PCT Filed: Nov. 19, 2018

(86) PCT No.: PCT/JP2018/042711
§ 371 (c)(1),
(2) Date: May 18, 2020

(87) PCT Pub. No.: WO2019/098373
PCT Pub. Date: May 23, 2019

(65) Prior Publication Data
US 2020/0360257 A1    Nov. 19, 2020

(30) Foreign Application Priority Data

Nov. 20, 2017  (JP) .............................. JP2017-223222

(51) Int. Cl.
*A61Q 5/02* (2006.01)
*A61Q 5/04* (2006.01)
*A61K 8/49* (2006.01)
*A61K 8/365* (2006.01)
*A61Q 5/12* (2006.01)

(52) U.S. Cl.
CPC ............ *A61K 8/4913* (2013.01); *A61K 8/365* (2013.01); *A61Q 5/02* (2013.01); *A61Q 5/04* (2013.01); *A61Q 5/12* (2013.01); *A61K 2800/30* (2013.01); *A61K 2800/43* (2013.01); *A61K 2800/522* (2013.01); *A61K 2800/59* (2013.01)

(58) Field of Classification Search
None
See application file for complete search history.

(56) References Cited

U.S. PATENT DOCUMENTS

| 5,352,443 | A | 10/1994 | Kubo et al. | |
|---|---|---|---|---|
| 2004/0016062 | A1 | 1/2004 | Plos | |
| 2010/0037404 | A1* | 2/2010 | Koike | A61K 8/894 8/423 |
| 2010/0125956 | A1* | 5/2010 | Koike | A61K 8/738/429 |
| 2015/0290096 | A1 | 10/2015 | Rose et al. | |
| 2016/0000671 | A1* | 1/2016 | Rose | A61K 8/922 424/70.13 |
| 2018/0263876 | A1* | 9/2018 | Furukawa | A61Q 5/04 |

FOREIGN PATENT DOCUMENTS

| EP | 0 342 034 B1 | 10/1993 |
|---|---|---|
| EP | 1 738 739 A1 | 1/2007 |
| JP | 5-271 039 A | 10/1993 |
| JP | 2003-286140 A | 10/2003 |
| JP | 2008-1676 A | 1/2008 |
| JP | 2009-137877 A | 6/2009 |
| JP | 2009-173574 A | 8/2009 |
| WO | WO 2014/067702 A1 | 5/2014 |
| WO | WO 2014/068102 A2 | 5/2014 |
| WO | WO 2017/081314 A1 | 5/2017 |

OTHER PUBLICATIONS

U.S. Appl. No. 16/765,061, filed May 18, 2020, Sakai, Yuta et al.
U.S. Appl. No. 16/765,033, filed May 18, 2020, Yoshida, Hiroshi et al.
U.S. Appl. No. 16/765,038, filed May 18, 2020, Shimazu, Ayako et al.
U.S. Appl. No. 16/765,067, filed May 18, 2020, Shimazu, Ayako et al.
Extended European Search Report dated Aug. 6, 2021 in European Patent Application No. 18877679.9, 8 pages.
International Search Report dated Feb. 5, 2019 in PCT/JP2018/042711 filed on Nov. 19, 2018, 1 page.
Dussaud, A. et al., "Progressive hair straightening using an automated flat iron: Function of silicones," Journal of Cosmetic Science, vol. 64, No. 2, Mar./Apr. 2013, pp. 119-131, 14 total pages.

* cited by examiner

*Primary Examiner* — Jyothsna A Venkat

(74) *Attorney, Agent, or Firm* — Oblon, McClelland, Maier & Neustadt, L.L.P.

(57) ABSTRACT

The present invention relates to a hair treatment method including the following step (i) and step (ii) in this order:

Step (i): a step of applying a composition containing the following component (A) on a hair:

(A) a compound represented by the following general formula (1) or a salt thereof:

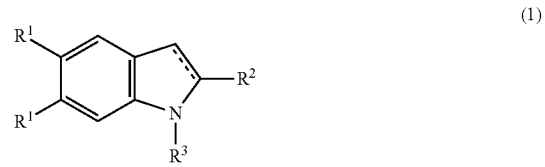

(1)

wherein a broken line represents the presence or absence of a π bond; $R^1$ represents a hydroxy group or an acetoxy group; $R^2$ represents a hydrogen atom or —COOR (R is a hydrogen atom, a methyl group, or an ethyl group); and $R^3$ represents a hydrogen atom, an acetyl group, a methyl group, or an ethyl group; and Step (ii): a step of giving a shape to the hair while applying a temperature of 140° C. or higher and 220° C. or lower to the hair.

11 Claims, No Drawings

HAIR TREATMENT METHOD

FIELD OF THE INVENTION

The present invention relates to a hair treatment method.

BACKGROUND OF THE INVENTION

In conventional permanent wave or hair straightening or the like, in order to permanently or semi-permanently keep a shape imparted to the hair, it is needed to denature a cortex protein which determines the shape of hair. As a method for denaturing the cortex protein, a method of adopting chemical denaturation with a reducing agent or a strong alkali having a pH of 12 to 14, which is blended in a permanent waving agent or an alkaline relaxer, is well known. However, it is also well known that according to such a method, since the bond of a protein in hair is cleaved, a burden on the hair protein is large, and a damage is liable to remain in the hair.

Then, a method for permanently keeping the shape given to the hair without adopting chemical denaturation with a reducing agent or a strong alkali and without cleaving the bond of the protein in hair is investigated.

As a method for correcting the wavy hair even during giving a shape to the hair, for example, PTL 1 describes that by treating the hair with a hair treatment agent containing an alkoxysilane, an organic acid, water, and a predetermined compound that is a melanin precursor, at the same time of dyeing the hair with a polymer of the melanin precursor, tension and stiffness are given to the hair by a polymer of a silanol compound produced through hydrolysis of the alkoxysilane, whereby an effect for improving collectivity of the hair and an effect for correcting the wavy hair are persistently obtained. In addition, NPL 1 describes that the wavy hair was irreversibly corrected by subjecting the hair to a hair iron treatment with a flat iron several times at temperatures of 144° C., 154° C., and 175° C.

CITATION LIST

Patent Literature

PTL 1: JP 2008-1676 A

Non-Patent Literature

NPL 1: Journal of Cosmetic Science, Vol. 64, pp. 119-131 (2013)

SUMMARY OF THE INVENTION

The present invention relates to a hair treatment method including the following step (i) and step (ii) in this order:

Step (i): a step of applying a composition containing the following component (A) on a hair:

(A) a compound represented by the following general formula (1) or a salt thereof:

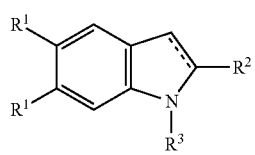

(1)

wherein a broken line represents the presence or absence of a π bond; $R^1$ represents a hydroxy group or an acetoxy group; $R^2$ represents a hydrogen atom or —COOR is a hydrogen atom, a methyl group, or an ethyl group); and $R^3$ represents a hydrogen atom, an acetyl group, a methyl group, or an ethyl group; and Step (ii): a step of giving a shape to the hair while applying a temperature of 140° C. or higher and 220° C. or lower to the hair.

DETAILED DESCRIPTION OF THE INVENTION

[Hair Treatment Method]

The hair treatment method of the present invention (hereinafter also referred to "method of the present invention") includes the following step (i) and step (ii) in this order:

Step (i): a step of applying a composition containing the following component (A) on a hair, (A) a compound represented by the following general formula (1) or a salt thereof:

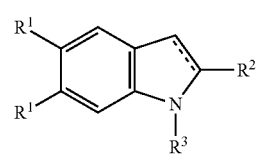

(1)

wherein a broken line represents the presence or absence of a π bond; $R^1$ represents a hydroxy group or an acetoxy group; $R^2$ represents a hydrogen atom or —COOR (R is a hydrogen atom, a methyl group, or an ethyl group); and $R^3$ represents a hydrogen atom, an acetyl group, a methyl group, or an ethyl group; and Step (ii): a step of giving a shape to the hair while applying a temperature of 140° C. or higher and 220° C. or lower to the hair.

In view of the fact that the method of the present invention includes the aforementioned predetermined step (i) and step (ii), there is brought such an effect that not only a shape is given to the hair without chemically denaturing the hair protein, but also the shape can be kept even after shampooing.

According to the methods described in PTL 1 and NPL 1, though the effect for correcting the wavy hair is perceived in its own way, there is a case where when shampooing or the like is repeated thereafter, the habit or wave of hair gradually returns to the original state. Thus, the methods described in PTL 1 and NPL 1 were not thoroughly satisfactory from the standpoint of keeping the shape given to the hair.

A problem of the present invention is to provide a hair treatment method capable of giving a shape to the hair without chemically denaturing a hair protein and keeping the shape even after shampooing.

The present inventor has found that the aforementioned problem can be solved by a hair treatment method including a step of applying a composition containing a predetermined melanin precursor on the hair; and a step of giving a shape to the hair at a temperature falling within a predetermined range in this order.

In accordance with the hair treatment method of the present invention, it is possible to give a shape to the hair without chemically denaturing a hair protein and to keep the shape even after shampooing.

The reason why the aforementioned effect is obtained by the method of the present invention may be considered to reside as follows. The component (A) is a melanin precursor, and when penetrating into the hair to cause oxidation polymerization, it becomes a melanin polymer (melanin pigment). It may be considered that this melanin polymer not only has a hair dyeing effect but also has an effect for keeping the shape given to the hair. Specifically, it may be considered that pseudo thermoplasticity is given to the hair containing the polymer of the component (A), and in the step (ii), the shape is given to the hair under a high-temperature condition, and as a result, the given hair shape is kept.

Then, it is estimated that when the step (i) is first performed to feed the component (A) that is the melanin precursor to the hair, and the step (ii) is then performed, the shape given to the hair is semi-permanently kept owing to thermoplasticity of the melanin polymer formed in the hair, whereby the shape of the hair becomes difficult to return to the original state even after shampooing.

(Step (i))

The step (i) is a step of applying a composition containing the following component (A) on a hair:

(A) a compound represented by the following general formula (1) or a salt thereof:

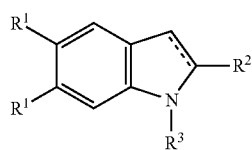

(1)

wherein a broken line represents the presence or absence of a π bond; $R^1$ represents a hydroxy group or an acetoxy group; $R^2$ represents a hydrogen atom or —COOR (R is a hydrogen atom, a methyl group, or an ethyl group); and $R^3$ represents a hydrogen atom, an acetyl group, a methyl group, or an ethyl group.

According to the step (i), the component (A) that is a melanin precursor is fed to the hair. The component (A) penetrates into the hair and then causes oxidation polymerization owing to air in the air, to form a melanin pigment (melanin polymer). When the component (A) is fed to the hair in the step (i), and then, the shape is given to the hair under a predetermined condition in the step (ii), a high shape-keeping effect is revealed.

Although the composition which is used in the step (i) is not particularly limited so long as it contains the component (A), examples thereof include a hair cleansing agent, such as a shampoo, a hair rinse, a hair conditioning agent, a hair treatment agent (inclusive of a non-washed away type), a hair styling agent, a hair dye, and a hair growth promoter. Of these, a hair rinse, a hair conditioning agent, a hair treatment agent, or a hair styling agent is preferred.

The formulation of the composition is not particularly limited, and it is possible to take an arbitrary formulation, for example, a liquid, a foam, a paste, a cream, a solid, and a powder. From the viewpoint of applicability on the hair, the formulation is preferably a liquid, a paste, or a cream.

<Component (A)>

The composition which is used in the step (i) contains the component (A) that is a compound represented by the following general formula (1) or a salt thereof. The component (A) is a melanin precursor which is polymerized through air oxidation and converted to a melanin polymer (melanin pigment). The foregoing polymer not only gives a high shape-keeping effect to the hair after the treatment but also acts as a dyeing agent of hair.

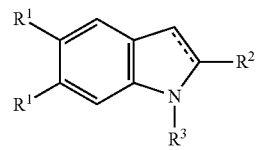

(1)

In the formula, a broken line represents the presence or absence of a π bond; $R^1$ represents a hydroxy group or an acetoxy group; $R^2$ represents a hydrogen atom or —COOR (R is a hydrogen atom, a methyl group, or an ethyl group); and $R^3$ represents a hydrogen atom, an acetyl group, a methyl group, or an ethyl group.

The melanin precursor of the component (A) is an indole derivative or an indoline derivative that is the compound represented by the general formula (1), or a salt thereof, and in the present invention, one or a combination of two or more thereof can be used. From the viewpoint of obtaining the effects of the present invention, the component (A) is more preferably an indole derivative (namely, a π bond exists in the broken line portion in the general formula (1)).

From the viewpoint of availability of the component (A) and giving a high shape-keeping effect to the hair after the treatment, in the general formula (1), $R^1$ is preferably a hydroxy group; $R^2$ is preferably a hydrogen atom or —COOR (R is a hydrogen atom, a methyl group, or an ethyl group), and more preferably a hydrogen atom or —COOH; and $R^3$ is preferably a hydrogen atom.

Examples of the compound represented by the general formula (1) include 5,6-dihydroxyindole, 5,6-dihydroxyindole-2-carboxylic acid, methyl 5,6-dihydroxyindole-2-carboxylate, ethyl 5,6-dihydroxyindole-2-carboxylate, N-methyl-5,6-dihydroxyindole, N-methyl-5,6-dihydroxyindole-2-carboxylic acid, N-ethyl-5,6-dihydroxyindole, N-ethyl-5,6-dihydroxyindole-2-carboxylic acid, N-acetyl-5,6-dihydroxyindole, N-acetyl-5,6-dihydroxyindole-2-carboxylic acid, 5-acetoxy-6-hydroxyindole, 5-acetoxy-6-hydroxyindole-2-carboxylic acid, 5,6-dihydroxyindoline, 5,6-dihydroxyindoline-2-carboxylic acid, methyl 5,6-dihydroxyindoline-2-carboxylate, ethyl 5,6-dihydroxyindoline-2-carboxylate, N-methyl-5,6-dihydroxyindoline, N-methyl-5,6-dihydroxyindoline-2-carboxylic acid, N-ethyl-5,6-dihydroxyindoline, N-ethyl-5,6-dihydroxyindoline-2-carboxylic acid, N-acetyl-5,6-dihydroxyindoline, N-acetyl-5,6-dihydroxyindoline-2-carboxylic acid, 5-acetoxy-6-hydroxyindoline, and 5-acetoxy-6-hydroxyindoline-2-carboxylic acid.

Examples of the salt of the compound represented by the general formula (1) include a hydrochloride, a hydrobromide, a sulfate, a phosphate, an acetate, a propionate, a lactate, and a citrate of the foregoing compounds. Above all, a hydrobromide is preferred from the viewpoint of availability and a shape-keeping effect of the hair after the treatment.

In the general formula (1), when $R^2$ is —COOH, examples of the salt of the compound represented by the general formula (1) include carboxylates thereof ($R^2$ is —COO$^-$X$^+$ (X$^+$ is a cation, such as an alkali metal ion, e.g., Na$^+$ and K$^+$, an alkaline earth metal ion, e.g., Ca$^+$ and Mg$^+$, and an ammonium ion)).

From the viewpoint of giving a high shape-keeping effect to the hair after the treatment and hair dyeing properties, the component (A) is preferably one or more selected from the group consisting of 5,6-dihydroxyindole, 5,6-dihydroxyindole-2-carboxylic acid, 5,6-dihydroxyindoline, and 5,6-dihydroxyindoline-2-carboxylic acid, and salts thereof; more preferably one or more selected from the group consisting of 5,6-dihydroxyindole, 5,6-dihydroxyindole-2-carboxylic acid, and 5,6-dihydroxyindoline hydrobromide; and still more preferably one or two selected from the group consisting of 5,6-dihydroxyindole and 5,6-dihydroxyindole-2-carboxylic acid. A combination of 5,6-dihydroxyindole and 5,6-dihydroxyindole-2-carboxylic acid is yet still more preferred from the viewpoint of a balance between the shape-keeping effect of the hair after the treatment and the hair dyeing properties.

In the case of use of a combination of 5,6-dihydroxyindole and 5,6-dihydroxyindole-2-carboxylic acid, a molar ratio thereof is preferably in a range of 50/50 to 99/1, more preferably in a range of 80/20 to 99/1, and still more preferably in a range of 85/15 to 95/5. When the molar ratio of 5,6-dihydroxyindole and 5,6-dihydroxyindole-2-carboxylic acid falls within the aforementioned range, the shape-keeping effect of the hair after the treatment and the hair dyeing properties are more improved.

The molar ratio of 5,6-dihydroxyindole and 5,6-dihydroxyindole-2-carboxylic acid can be quantitatively determined by means of reversed phase HPLC.

From the viewpoint of the shape-keeping effect of the hair after the treatment and the hair dyeing properties, the content of the component (A) in the composition is preferably 0.02% by mass or more, more preferably 0.05% by mass or more, and still more preferably 0.1% by mass or more, and from the viewpoint of economy, it is preferably 5% by mass or less, more preferably 3% by mass or less, still more preferably 2% by mass or less, and yet still more preferably 1% by mass or less.

[Alkaline Agent]

It is preferred that the composition which is used in the step (i) contains an alkaline agent. The alkaline agent has not only an action to swell the hair, thereby opening the cuticle and penetrating the component (A) into the interior of the hair, but also an action to promote a polymerization reaction of the component (A) in the hair, thereby improving the hair dyeing properties and the shape-keeping effect of the hair. As the alkaline agent, any material can be used without particular limitations so long as it is an alkaline agent that is used for usual hair dyes.

Examples of the alkaline agent include ammonia; alkanolamines, such as mono-, di-, or tri-methanolamine and mono-, di-, or tri-ethanolamine; alkylamines, such as methylamine, dimethylamine, ethylamine, diethylamine, N-methylethylamine, propylamine, and butylamine; aralkylamine, such as benzylamine; and inorganic alkali compounds, such as sodium hydroxide and potassium hydroxide, and one or more of these materials can be used. The carbon number of the alkanolamine, alkylamine, or aralkylamine is preferably 10 or less, and more preferably 8 or less from the viewpoint of water solubility.

Above all, from the viewpoint of penetrating the component (A) into the interior of the hair, the alkaline agent is preferably one or more selected from the group consisting of ammonia, an alkanolamine, an alkylamine, an aralkylamine, sodium hydroxide, and potassium hydroxide. The alkaline agent more preferably contains one or more of ammonia and an alkanolamine, still more preferably contains a monoalkanolamine, and yet still more preferably contains monoethanolamine.

From the viewpoint of not only penetrating the component (A) and the like into the interior of the hair but also promoting a polymerization reaction of the component (A) in the hair, thereby improving the hair dyeing properties and the shape-keeping effect of the hair, the content of the alkaline agent in the composition is preferably 0.01% by mass or more, more preferably 0.1% by mass or more, and still more preferably 0.5% by mass or more, and from the viewpoint of suppressing irritation, it is preferably 10% by mass or less, more preferably 7.5% by mass or less, and still more preferably 5% by mass or less.

[pH Adjustor]

From the viewpoint of adjusting the pH to an optimum range for polymerization of the component (A), thereby promoting the polymerization reaction of the component (A) in the hair and giving the high shape-keeping effect to the hair after the treatment, the composition which is used in the step (i) can contain a pH adjustor. In the case where the composition which is used in the step (i) contains the aforementioned alkaline agent, a protonating agent is preferred as the pH adjustor which is used in the present invention. The protonating agent may be any of a monobasic acid and a polybasic acid, and may be any of an organic acid (the carbon number is 1 or more and 8 or less, provided that ascorbic acid is excluded) and an inorganic acid. As the protonating agent, one or more selected from the group consisting of hydrochloric acid, sulfuric acid, phosphoric acid, formic acid, acetic acid, and citric acid are exemplified, and one or two selected from the group consisting of phosphoric acid and citric acid are more preferred.

In the case of using the pH adjustor, though the content thereof is not particularly limited so long as it is an amount at which the pH of the composition can be adjusted to a desired range, it is preferably 0.05% by mass or more, more preferably 0.1% by mass or more, and still more preferably 0.2% by mass or more. In addition, from the viewpoint of formulation stability, the content of the pH adjustor is preferably 5.0% by mass or less, more preferably 4.0% by mass or less, and still more preferably 3.5% by mass or less.

[pH]

From the viewpoint of not only penetrating the component (A) and the like into the interior of the hair but also promoting a polymerization reaction of the component (A) in the hair, thereby giving the high shape-keeping effect to the hair after the treatment and the viewpoint of improvement in hair dyeing properties, the pH of the composition which is used in the step (i) is preferably 8.0 or more, more preferably 8.5 or more, and still more preferably 9.0 or more. This is because the component (A) that is the melanin precursor reacts with oxygen in air under a basic condition, whereby it is liable to be polymerized. From the viewpoint of the shape-keeping effect of the hair after the treatment and the viewpoint of improvement in hair dyeing properties and suppressing any damage to the hair, the foregoing pH is preferably 12.0 or less, more preferably 11.0 or less, and still more preferably 10.5 or less.

The aforementioned pH is a measured value at 25° C., and specifically, it can be measured by a method described in the section of Examples.

[Antioxidant]

It is preferred that the composition which is used in the step (i) contains an antioxidant. When the antioxidant is contained, the oxidation polymerization of the component (A) which is caused in sites other than the inside of the hair can be suppressed, and therefore, the shape-keeping effect of the hair after the treatment is more improved.

Examples of the antioxidant include sulfurous acid, ascorbic acid, L-cysteine, and N-acetyl-L-cysteine, and salts thereof. From the viewpoint of stabilization of the component (A), the shape-keeping effect of the hair after the treatment, and improvement in hair dyeing properties, one or more selected from the group consisting of sulfurous acid, and ascorbic acid and salts thereof are preferred.

In the case of using the antioxidant, the content thereof in the composition is preferably 0.05% by mass or more, more preferably 0.1% by mass or more, still more preferably 0.5% by mass or more, and yet still more preferably 0.8% by mass or more, and it is preferably 10% by mass or less, more preferably 5% by mass or less, and still more preferably 2% by mass or less.

[Aqueous Medium]

The composition which is used in the step (i) typically contains an aqueous medium. Examples of the aqueous medium include water; a lower alcohol, such as ethanol and isopropyl alcohol; and a low-molecular diol or triol having 6 or less carbon atoms, such as 1,3-butylene glycol, glycerin, ethylene glycol, and propylene glycol, with water being preferred. In the case of using water as the aqueous medium, from the viewpoint of easiness of applying the composition on the hair, stability in the case of being formed in an emulsified state, and the shape-keeping effect of the hair, the content of water in the composition is preferably 50% by mass or more, more preferably 60% by mass or more, and still more preferably 70% by mass, and it is preferably 95% by mass or less, and more preferably 90% by mass or less.

The composition which is used in the step (i) may appropriately contain, in addition to the component (A), a component which is typically used for hair cosmetics or hair dyes, within a range where the purpose of the present invention is not impaired. Examples of the foregoing component include a dyeing agent other than the component (A), a surfactant, a polymer, a silicone, an aromatic alcohol, an oil, an anti-dandruff agent, a vitamin compound, a disinfectant, an antiinflammatory agent, an antiseptic, a chelating agent, a humectant, a pearlescent agent, a ceramide, a perfume, and an ultraviolet absorber.

[Dyeing Agent Other than Component (A)]

The composition which is used in the step (i) may further contain a dyeing agent other than the component (A). Examples of the foregoing dyeing agent include an oxidation dye (constituted of a precursor and a coupler) and a direct dye, each of which is typically used for hair dyes.

As the dying agent other than the component (A), one or more materials can be used. Among the foregoing dyeing agents, paraphenylenediamine, toluene-2,5-diamine, paraaminophenol, 4-aminometacresol, 1-hydroxyethyl-4,5-diaminopyrazole, and salts thereof are preferred as the precursor constituting the oxidation dye; and 2,4-diaminophenoxyethanol, metaaminophenol, 2-methyl-5-aminophenol, resorcin, 2-methylresorcin, 4-chlororesorcinol, 1-naphthol, 2-amino-3-hydroxypyridine, 2-amino-4-(6-hydroxyethyl)aminoanisole, and salts thereof are preferred as the coupler.

In the case of using the dyeing agent other than the component (A), from the viewpoint of improvement in dyeing properties, the content thereof is preferably 0.01% by mass or more, and more preferably 0.02% by mass or more, and from the viewpoint of the shape-keeping effect of the hair after the treatment, it is preferably 1% by mass or less, and more preferably 0.5% by mass or less.

From the viewpoint of giving the high shape-keeping effect to the hair after the treatment, the content of the dyeing agent other than component (A) in the composition is still more preferably 0.05% by mass or less, yet still more preferably 0.03% by mass or less, and even yet still more preferably 0.01% by mass or less, and it is even still more preferred that the dyeing agent other than the component (A) is not substantially contained.

[Surfactant]

The composition which is used in the step (i) may further contain a surfactant. When the surfactant is contained, in the case where the foregoing composition is a hair cosmetic, its effect can be effectively revealed. Examples of the surfactant include an anionic surfactant, a cationic surfactant, an ampholytic surfactant, and a nonionic surfactant. In the case of using the surfactant, when the composition is a hair treatment agent, a hair styling agent, or a hair dye, it preferably contains at least a nonionic surfactant; and when the composition is a hair rinse or a hair conditioning agent, it preferably contains at least a cationic surfactant. In addition, when the composition is a hair cleansing agent, such as a shampoo, it is preferred that the composition contains at least an anionic surfactant and further contains an ampholytic surfactant.

[Polymer]

The composition which is used in the step (i) can contain a polymer. As the polymer, one or more selected from the group consisting of an anionic polymer, a cationic polymer, and a nonionic polymer can be appropriately selected and used according to an application of the composition or required properties or performance. For example, in the case where the composition is an agent for giving a shape, such as a styling agent, from the viewpoint of forming a film on the surface of the hair to give shape-keeping properties, it is preferred that the composition contains an anionic polymer.

<<Anionic Polymer>>

From the viewpoint of making the applicability favorable and from the viewpoint of forming a film on the surface of the hair to make the touch of the hair favorable, the anionic polymer which is used in the present invention is preferably a polymer (a) containing a structural unit represented by the following general formula (3) (hereinafter also referred to simply as "polymer (a)").

(3)

In the formula, $R^4$ represents a hydrogen atom or a carboxy group; and W represents a hydrogen atom or a methyl group.

Although the polymer (a) containing the structural unit represented by the general formula (3) may contain other structural unit, from the viewpoint of making the applicability favorable and the viewpoint of making the touch of the hair favorable, the content of the structural unit represented by the general formula (3) in the polymer is preferably 20% by mass or more, more preferably 40% by mass or more, still more preferably 50% by mass or more, and yet still more preferably 70% by mass or more. In addition, an upper limit thereof is 100% by mass.

A weight average molecular weight of the anionic polymer is typically in a range of 1,000 to 1,000,000, preferably 10,000 or more, and more preferably 20,000 or more, and it is preferably 500,000 or less, and more preferably 200,000 or less. The foregoing weight average molecular weight is a molecular weight expressed in terms of polyethylene glycol as measured by gel filtration chromatography (GPC).

Among commercially available anionic polymers, specific examples of the polymer (a) include a carboxy vinyl polymer, such as CARBOPOL 980 and 981 (all of which are manufactured by Lubrizol Advanced Materials, Inc.); a (meth)acrylic acid/(meth)acrylic acid ester copolymer, such as DIAHOLD (manufactured by Mitsubishi Chemical Corporation); an (alkyl acrylate/diacetone acrylamide) copolymer AMP, such as PLUS SIZE L-53P, L-75CB, L-9540B, L-6466, and L-3200B (all of which are manufactured by Goo Chemical Co., Ltd.); an acrylic acid/alkyl acrylate/alkyl acrylamide copolymer, such as ULTRAHOLD 8 and ULTRAHOLD STRONG (all of which are manufactured by BASF SE), and AMPHOMER V-42 (manufactured by National Starch); and a polyvinylpyrrolidone/acrylate/(meth)acrylic acid copolymer, such as LUVIFLEX VBM35 (manufactured by BASF SE).

In the case of containing the polymer in the composition which is used in the step (i), from the viewpoint of improvement in hair dyeing properties, and in the case of the anionic polymer, from the viewpoint of making applicability favorable and the viewpoint of making the touch of the hair favorable, the content of the polymer in the composition is preferably 0.001% by mass or more, more preferably 0.005% by mass or more, still more preferably 0.01% by mass or more, and yet still more preferably 0.05% by mass or more, and it is preferably 10% by mass or less, more preferably 5% by mass or less, still more preferably 3% by mass or less, and yet still more preferably 1% by mass or less.

[Application Step]

In the step (i), a step of applying the aforementioned composition on the hair (hereinafter also referred to as "application step") is performed. By performing the application step, the component (A) is penetrated into the hair, whereby the shape-keeping effect can be given to the hair after the treatment.

Although the composition may be applied on the dried hair or may be applied on the wet hair, from the viewpoint of firmly giving the shape to the hair, it is preferred to apply the composition to the dried hair.

A method for applying the composition is not particularly limited, and examples thereof include a method of using hands, such as rubbing of the composition into the hair, and combing fingers through the hair; a method of using a tool, such as a brush, a comb, and a brush; and a combination of the both.

From the viewpoint of giving the shape to the hair under a heating condition in the step (ii) as mentioned later, the application step is preferably performed at a temperature lower than that in the step (ii), and it is performed at a temperature of preferably 40° C. or lower, and more preferably 35° C. or lower. Although a lower limit value of the temperature in the application step is not particularly limited, from the viewpoint of penetrating the component (A) in the composition into the hair, to enhance the shape-keeping effect of the hair after the treatment, the application step is performed at a temperature of preferably 5° C. or higher, and more preferably 10° C. or higher.

From the viewpoint of penetrating the component (A) in the composition into the hair, to enhance the shape-keeping effect of the hair after the treatment, the amount of the composition to be applied on the hair in the step (i) is preferably 0.05 or more, more preferably 0.1 or more, and still more preferably 0.25 or more in terms of a bath ratio to the mass of hair [(mass of composition)/(mass of hair)]; and from the viewpoint of suppressing dripping down of the composition from the hair and penetrating the component (A) into the hair, to enhance the shape-keeping effect of the hair after the treatment, it is preferably 1.5 or less, and more preferably 1.25 or less. The hair that is an object of the treatment may be at least a part of hair of head.

From the viewpoint of penetrating the component (A) in the composition into the hair, to enhance the shape-keeping effect of the hair after the treatment, it is preferred that the method of the present invention includes a step of allowing the hair in a state where the aforementioned composition is applied, to stand for 1 minute or more between the step (i) and the step (ii).

From the viewpoint of penetrating the component (A) in the composition into the hair, the standing time is more preferably 3 minutes or more, and still more preferably 5 minutes or more. In addition, from the viewpoint of effectively performing the treatment, the standing time is preferably 30 minutes or less.

It is preferred to perform the step of allowing the hair to stand immediately after the step (i) and before the step (ii).

From the viewpoint of giving the shape to the hair under a heating condition in the step (ii) as mentioned later, the step of allowing the hair to stand is preferably performed at a temperature lower than that in the step (ii), and it is performed at a temperature of preferably 40° C. or lower, and more preferably 35° C. or lower. Although a lower limit value of the temperature in the step of allowing the hair to stand is not particularly limited, from the viewpoint of penetrating the component (A) in the composition into the hair, to enhance the shape-keeping effect of the hair after the treatment, the step of allowing the hair to stand is performed at a temperature of preferably 5° C. or higher, and more preferably 10° C. or higher.

From the viewpoint of removing a residue of the composition which has been applied on the hair, to enhance the shape-keeping effect of the hair after the treatment, it is preferred that the method of the present invention includes a step of rinsing the hair (hereinafter also referred to as "rinsing step") between the step (i) and the step (ii). In the rinsing step, for example, an operation in which the composition which has been applied on the hair in the step (i) is washed away with water is performed. In the case of performing the step of allowing the hair to stand, it is preferred to perform the rinsing step thereafter.

After performing the rinsing step, a step of cleansing the hair with a hair cleansing agent or the like may be further performed before the step (ii) as mentioned later.

From the viewpoint of firmly giving the shape to the hair in the step (ii), it is preferred that a step of drying the hair is performed after the rinsing step and before the step (ii).

(Step (ii))

The step (ii) is a step of giving a shape to the hair while applying a temperature of 140° C. or higher and 220° C. or lower to the hair. In view of the fact that the shape is given to the hair at this temperature, there is brought such an effect that not only a shape is given to the hair without chemically denaturing the hair protein, but also the shape can be kept even after shampooing. Specifically, in view of the fact that the component (A) which has been penetrated into the hair in the step (i) causes oxidation polymerization in the hair, it may be considered that pseudo thermoplasticity is given to the hair containing the foregoing polymer, and in the step (ii), the shape is given to the hair under a high-temperature condition, and as a result, the given hair shape is semi-permanently kept. In addition, from the viewpoint of suppressing a damage of the hair, the temperature of the step (ii) is 220° C. or lower.

From the viewpoint of firmly giving the shape to the hair, the temperature during giving the shape to the hair in the step (ii) is preferably 160° C. or higher, more preferably 180° C. or higher, and still more preferably 190° C. or higher.

From the viewpoint of firmly giving the shape to the hair, it is preferred that the step of giving the shape to the hair in the step (ii) (hereinafter also referred to as "shape-giving step") is performed on the dried hair. Although the shape-keeping method is not particularly limited, it is preferred to give the shape while at least applying a tension to the hair at the aforementioned temperature, The shape to be given to the hair in the step (ii) is not particularly limited, and it may be a shape different from that of the hair before giving the shape in the step (ii). For example, a curl shape may be given to the straight hair, and a wave-relaxed shape may be given to a wavy hair. Here, the "wave-relaxed shape" means that the wavy shape is stretched to approach to a straight shape, and a degree thereof is not limited but also includes a straight shape.

Above all, the step (ii) in the present invention is preferably a step of giving a wave-relaxed shape to the wavy hair while applying the aforementioned temperature from the root of the hair toward the hair end direction.

The shape-giving step can be, for example, performed by using a hair iron. Specifically, examples thereof include a method of holding the hair with a hair iron set to a temperature of 140° C. or higher and 220° C. or lower and giving the shape to the hair while sliding the hair iron from the root of the hair toward the hair end direction to stretch the hair. For example, in the case of using a flat-type hair iron, when sliding it straight toward the hair end direction, the wave-refaxed shape of the hair can be given, whereas when holding the hair with a hair iron and sliding the hair iron while winding therearound, the curl shape can be given.

According to the hair treatment method of the present invention, it is possible to semi-permanently give the shape to the hair by means of a principle quite different from permanent treatment with a reducing agent or treatment with a strongly alkaline hair treatment agent, each of which chemically denatures the hair protein. In consequence, the hair treatment method of the present invention does not include a step of applying to the hair a hair treatment agent containing a reducing agent or a hair treatment agent having a pH of more than 12. For that reason, according to the hair treatment method of the present invention, not only the shape can be given to the hair without causing a damage, but also even when shampooing is performed thereafter, the shape does not completely return to the original state, and the shape can be kept.

Regarding the aforementioned embodiments, the present invention discloses the following hair treatment methods.

<1> A hair treatment method including the following step (i) and step (ii) in this order:

Step (i): a step of applying a composition containing 0.05% by mass or more and 3% by mass or less of the following component (A) on the hair:

(A) a compound represented by the following general formula (1) or a salt thereof:

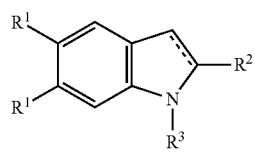

(1)

wherein a broken line represents the presence or absence of a π bond; $R^1$ represents a hydroxy group or an acetoxy group; $R^2$ represents a hydrogen atom or —COOR (R is a hydrogen atom, a methyl group, or an ethyl group); and $R^3$ represents a hydrogen atom, an acetyl group, a methyl group, or an ethyl group; and Step (ii): a step of giving a shape to the hair while applying a temperature of 180° C. or higher and 220° C. or lower to the hair.

<2> A hair treatment method including the following step (1) and step (ii) in this order:

Step (i): a step of applying a composition containing 0.05% by mass or more and 3% by mass or less of the following component (A) on the hair:

(A) a compound represented by the following general formula (1) or a salt thereof:

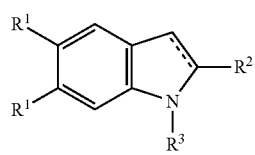

(1)

wherein a broken line represents the presence or absence of a π bond; $R^1$ represents a hydroxy group or an acetoxy group; $R^2$ represents a hydrogen atom or —COOR (R is a hydrogen atom, a methyl group, or an ethyl group); and $R^3$ represents a hydrogen atom, an acetyl group, a methyl group, or an ethyl group; and Step (ii): a step of giving a wave-relaxed shape to a wavy hair while applying a temperature of 140° C. or higher and 220° C. or lower from the root of the hair toward the hair end direction.

<3> A hair treatment method including the following step (i) and step (ii) in this order:

Step (i): a step of applying a composition containing 0.05% by mass or more and 3% by mass or less of the following component (A) on the hair:

(A) a compound represented by the following general formula (1) or a salt thereof:

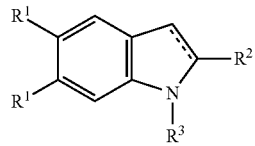

(1)

wherein a broken line represents the presence or absence of a π bond; $R^1$ represents a hydroxy group or an acetoxy group; R² represents a hydrogen atom or —COOR (R is a hydrogen atom, a methyl group, or an ethyl group); and R³ represents a hydrogen atom, an acetyl group, a methyl group, or an ethyl group; and Step (ii): a step of holding the hair with a hair iron set to a temperature of 140° C. or higher and 220° C. or lower and giving a shape to the hair while sliding the hair iron from the root of the hair toward the hair end direction to stretch the hair.

<4> The hair treatment method as set forth in any one of <1> to <3>, wherein a pH of the composition is 8.0 or more and 12.0 or less.

<5> The hair treatment method as set forth in any one of <1> to <4>, wherein the composition contains an antioxidant.

<6> The hair treatment method as set forth in any one of <1> to <5>, wherein the content of the component (A) in the composition is 0.1% by mass or more and 1% by mass or less.

<7> The hair treatment method as set forth in any one of <1> to <6>, wherein the amount of the composition to be applied on the hair in the step (i) is 0.05 or more and 1.5 or less in terms of a bath ratio to the mass of hair [(mass of composition)/(mass of hair)].

<8> The hair treatment method as set forth in any one of <1> to <7>, including a step of allowing the hair in a state where the composition is applied, to stand for 1 minute or more between the step (i) and the step (ii).

<9> The hair treatment method as set forth in any one of <1> to <8>, including a step of rinsing the hair between the step (i) and the step (ii).

<10> The hair treatment method as set forth in any one of <1> to <9>, wherein the composition is a hair cleansing agent, a hair rinse, a hair conditioning agent, a hair treatment agent, a hair styling agent, a hair dye, or a hair growth promoter.

<11> A hair treatment method including the following step (i) and step (ii) in this order:

Step (i): a step of applying a composition containing 0.1% by mass or more and 1% by mass or less of the following component (A) and having a pH of 8.0 or more and 12.0 or less on the hair:

(A) a compound represented by the following general formula (1) or a salt thereof:

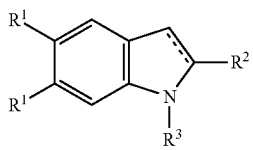

(1)

wherein a broken line represents the presence or absence of a π bond; R¹ represents a hydroxy group or an acetoxy group; R² represents a hydrogen atom or —COOR is a hydrogen atom, a methyl group, or an ethyl group); and R³ represents a hydrogen atom, an acetyl group, a methyl group, or an ethyl group; and Step (ii): a step of giving a shape to the hair while applying a temperature of 180° C. or higher and 220° C. or lower to the hair.

<12> A hair treatment method including the following step (i) and step (ii) in this order:

Step (i): a step of applying a composition containing 0.1% by mass or more and 1% by mass or less of the following component (A) and having a pH of 8.0 or more and 12.0 or less in an amount of 0.25 or more and 1.5 or less in terms of a bath ratio to the mass of hair [(mass of composition)/(mass of hair)] on the hair:

(A) a compound represented by the following general formula (1) or a salt thereof:

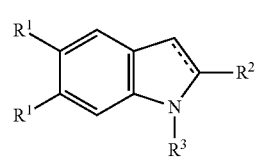

(1)

wherein a broken line represents the presence or absence of a π bond; R¹ represents a hydroxy group or an acetoxy group; R² represents a hydrogen atom or —COOR (R is a hydrogen atom, a methyl group, or an ethyl group); and R³ represents a hydrogen atom, an acetyl group, a methyl group, or an ethyl group; and Step (ii): a step of giving a shape to the hair while applying a temperature of 180° C. or higher and 220° C. or lower to the hair.

<13> A hair treatment method including the following step (i) and step (ii) in this order:

Step (i): a step of applying a composition containing 0.1% by mass or more and 1% by mass or less of the following component (A), having the content of a dyeing agent other than the component (A) of 0.03% by mass or less, and having a pH of 8.0 or more and 12.0 or less on the hair:

(A) a compound represented by the following general formula (1) or a salt thereof:

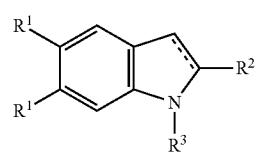

(1)

wherein a broken line represents the presence or absence of a π bond; R¹ represents a hydroxy group or an acetoxy group; R² represents a hydrogen atom or —COOR (R is a hydrogen atom, a methyl group, or an ethyl group); and R³ represents a hydrogen atom, an acetyl group, a methyl group, or an ethyl group; and Step (ii): a step of giving a shape to the hair while applying a temperature of 180° C. or higher and 220° C. or lower to the hair.

<14> A hair treatment method including the following step (i) and step (ii) in this order:

Step (i): a step of applying a composition containing 0.1% by mass or more and 1% by mass or less of (A) one or more selected from the group consisting of 5,6-dihydroxyindole, 5,6-dihydroxyindole-2-carboxylic acid, and 5,6-dihydroxyindoline hydrobromide and having a pH of 8.0 or more and 12.0 or less on the hair; and Step (ii): a step of giving a shape to the hair while applying a temperature of 180° C. or higher and 220° C. or lower to the hair.

<15> A hair treatment method including the following step (i) and step (ii) in this order and including, between the step (i) and the step (ii), a step of allowing the hair in a state where the composition is applied, to stand at a temperature of 10° C. or higher and 40° C. or lower for 1 minute or more and 30 minutes or less and a step of rinsing the hair:

Step (i): a step of applying a composition containing 0.1% by mass or more and 1% by mass or less of the following component (A) and having a pH of 8.0 or more and 12.0 or less on the hair:

(A) a compound represented by the following general formula (1) or a salt thereof:

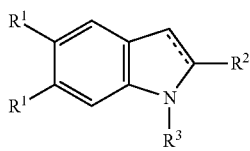

(1)

wherein a broken line represents the presence or absence of a π bond; $R^1$ represents a hydroxy group or an acetoxy group; $R^2$ represents a hydrogen atom or —COOR (R is a hydrogen atom, a methyl group, or an ethyl group); and $R^3$ represents a hydrogen atom, an acetyl group, a methyl group, or an ethyl group; and Step (ii): a step of giving a shape to the hair while applying a temperature of 180° C. or higher and 220° C. or lower to the hair.

<16> A hair treatment method including the following step (i) and step (ii) in this order and including, between the step (i) and the step (ii), a step of allowing the hair in a state where the composition is applied, to stand at a temperature of 10° C. or higher and 40° C. or lower for 1 minute or more and 30 minutes or less and a step of rinsing the hair:

Step (i): a step of applying a composition containing 0.1% by mass or more and 1% by mass or less of (A) one or more selected from the group consisting of 5,6-dihydroxyindole and 5,6-dihydroxyindole-2-carboxylic acid, having the content of a dyeing agent other than the component (A) of 0.03% by mass or less, and having a pH of 8.0 or more and 12.0 or less on the hair; and Step (ii): a step of giving a shape to the hair while applying a temperature of 180° C. or higher and 220° C. or lower to the hair.

<17> A hair treatment method including the following step (i) and step (ii) in this order and including, between the step (i) and the step (ii), a step of allowing the hair in a state where the composition is applied, to stand at a temperature of 10° C. or higher and 40° C. or lower for 1 minute or more and 30 minutes or less and a step of rinsing the hair:

Step (i): a step of applying a composition containing 0.1% by mass or more and 1% by mass or less of (A) one or more selected from the group consisting of 5,6-dihydroxyindole and 5,6-dihydroxyindole-2-carboxylic acid, having the content of a dyeing agent other than the component (A) of 0.03% by mass or less, and having a pH of 8.0 or more and 12.0 or less on the hair; and Step (ii): a step of giving a wave-relaxed shape to a wavy hair while applying a temperature of 180° C. or higher and 220° C. or lower from the root of the hair toward the hair end direction.

<18> A hair treatment method including the following step (i) and step (ii) in this order and including, between the step (i) and the step (ii), a step of allowing the hair in a state where the composition is applied, to stand at a temperature of 10° C. or higher and 40° C. or lower for 1 minute or more and 30 minutes or less and a step of rinsing the hair:

Step (i): a step of applying a composition containing 0.1% by mass or more and 1% by mass or less of (A) one or more selected from the group consisting of 5,6-dihydroxyindole and 5,6-dihydroxyindole-2-carboxylic acid, having the content of a dyeing agent other than the component (A) of 0.03% by mass or less, and having a pH of 8.0 or more and 12.0 or less on the hair; and Step (ii): a step of holding the hair with a hair iron set to a temperature of 180° C. or higher and 220° C. or lower and giving a shape to the hair while sliding the hair iron from the root of the hair toward the hair end direction to stretch the hair.

<19> A hair treatment method including the following step (i) and step (ii) in this order and including, between the step (i) and the step (ii), a step of allowing the hair in a state where the composition is applied, to stand at a temperature of 10° C. or higher and 40° C. or lower for 1 minute or more and 30 minutes or less, a step of rinsing the hair, and a step of drying the hair with a dryer:

Step (i): a step of applying a composition containing 0.1% by mass or more and 1% by mass or less of the following component (A) and having a pH of 8.0 or more and 12.0 or less on the hair:

(A) a compound represented by the following general formula (1) or a salt thereof:

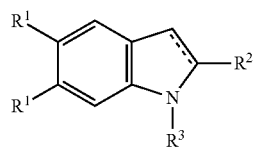

(1)

wherein a broken line represents the presence or absence of a π bond; $R^1$ represents a hydroxy group or an acetoxy group; $R^2$ represents a hydrogen atom or —COOR (R is a hydrogen atom, a methyl group, or an ethyl group); and $R^3$ represents a hydrogen atom, an acetyl group, a methyl group, or an ethyl group; and Step (ii): a step of giving a shape to the hair while applying a temperature of 180° C. or higher and 220° C. or lower to the hair.

<20> A hair treatment method including the following step (i) and step (ii) in this order and including, between the step (1) and the step (ii), a step of allowing the hair in a state where the composition is applied, to stand at a temperature of 10° C. or higher and 40° C. or lower for 1 minute or more and 30 minutes or less, a step of rinsing the hair, and a step of drying the hair with a dryer:

Step (i): a step of applying a composition containing 0.1% by mass or more and 1% by mass or less of (A) one or more selected from the group consisting of 5,6-dihydroxyindole and 5,6-dihydroxyindole-2-carboxylic acid, having the content of a dyeing agent other than the component (A) of 0.03% by mass or less, and having a pH of 8.0 or more and 12.0 or less on the hair; and Step (ii): a step of giving a shape to the hair while applying a temperature of 180° C. or higher and 220° C. or lower to the hair.

<21> A hair treatment method including the following step (i) and step (ii) in this order and including, between the step (i) and the step (ii), a step of allowing the hair in a state where the composition is applied, to stand at a temperature of 10° C. or higher and 40° C. or lower for 1 minute or more and 30 minutes or less, a step of rinsing the hair, and a step of drying the hair with a dryer:

Step (i): a step of applying a composition containing 0.1% by mass or more and 1% by mass or less of (A) one or more selected from the group consisting of 5,6-dihydroxyindole and 5,6-dihydroxyindole-2-carboxylic acid, having the content of a dyeing agent other than the component (A) of 0.03% by mass or less, and having a pH of 8.0 or more and 12.0 or less on the hair; and Step (ii): a step of giving a wave-relaxed shape to a wavy hair while applying a temperature of 180° C. or higher and 220° C. or lower from the root of the hair toward the hair end direction.

<22> A hair treatment method including the following step (i) and step (ii) in this order and including, between the step (i) and the step (ii), a step of allowing the hair in a state where the composition is applied, to stand at a temperature of 10° C. or higher and 40° C. or lower for 1 minute or more and 30 minutes or less, a step of rinsing the hair, and a step of drying the hair with a dryer:

Step (i): a step of applying a composition containing 0.1% by mass or more and 1% by mass or less of (A) one or more selected from the group consisting of 5,6-dihydroxyindole and 5,6-dihydroxyindole-2-carboxylic acid, having the content of a dyeing agent other than the component (A) of 0.03% by mass or less, and having a pH of 8.0 or more and 12.0 or less on the hair; and Step (ii): a step of holding the hair with a hair iron set to a temperature of 180° C. or higher and 220° C. or lower and giving a shape to the hair while sliding the hair iron from the root of the hair toward the hair end direction to stretch the hair.

EXAMPLES

The present invention is hereunder described by reference to Examples, but it should be construed that the present invention is not limited to the scope of the Examples.

[pH Measurement]

A pH of the composition for hair treatment at 25° C. was measured with a pH meter (F-51, manufactured by HORIBA, Ltd.).

[Preparation of Composition]

Compositions A to H for hair treatment that are a hair cosmetic were prepared by the following method. Each of the prepared compositions was stored in a nitrogen atmosphere, fractionated just before being applied on the hair, and then, subjected to evaluations as mentioned later.

Production Example 1 (Preparation of Composition A)

Among the components shown in Table 1, other components than a solution (A1), sodium sulfite, and ascorbic acid were mixed and uniformly dissolved. Subsequently, to the prepared solution, the solution (A1), sodium sulfite, and ascorbic acid were added in a nitrogen atmosphere, to prepare a composition A.

Production Example 2 (Preparation of Composition B [for Comparison])

A composition B was prepared in the same manner as in Production Example 1, except that in Production Example 1, the solution (A1) was not added.

Production Example 3 (Preparation of Composition C)

A composition C was prepared in the same manner as in Production Example 1, except that in Production Example 1, phosphoric acid was not added, and a moderate amount of monoethanolamine was added such that the pH of the composition was 7.

Production Example 4 (Preparation of Composition D)

A composition D was prepared in the same manner as in Production Example 1, except that in Production Example 1, ascorbic acid was not added.

Production Examples 5 to 6 (Preparation of Compositions E and F)

Compositions E and F were prepared in the same manner as in Production Example 1, except that in Production Example 1, a solution (A2) or a solution (A3) as mentioned later was used in place of the solution (A1).

Production Examples 7 to 8 (Preparation of Compositions G and H)

Among the components shown in Table 1, other components than the solution (A1), sodium sulfite, and ascorbic acid were mixed and uniformly dissolved. At this time, with respect to a composition G, an oxidation dye X as mentioned later was added, and with respect to a composition H, an oxidation dye Y as mentioned later was added. Subsequently, to each of the prepared solutions, the solution (A1), sodium sulfite, and ascorbic acid were added in a nitrogen atmosphere, to prepare compositions G and H.

TABLE 1

| Production example | | 1 | 2 | 3 | 4 | 5 | 6 | 7 | 8 |
|---|---|---|---|---|---|---|---|---|---|
| Composition | | A | B | C | D | E | F | G | H |
| (A1) 5,6-Dihydroxyindole solution [1] | % by mass | 25.00 | | 25.00 | 25.00 | | | 25.00 | 25.00 |
| (A2) 5,6-Dihydroxyindole solution [2] | | | | | | 25.00 | | | |
| (A3) 5,6-Dihydroxyindoline•HBr solution [3] | | | | | | | 25.00 | | |
| Oxidation dye X [4] | | | | | | | | 0.035 | |
| Oxidation dye Y [5] | | | | | | | | | 0.035 |
| Ascorbic acid [6] | | 0.6 | 0.6 | 0.6 | — | 0.6 | 0.6 | 0.6 | 0.6 |

TABLE 1-continued

| Production example | | 1 | 2 | 3 | 4 | 5 | 6 | 7 | 8 |
|---|---|---|---|---|---|---|---|---|---|
| Composition | | A | B | C | D | E | F | G | H |
| Sodium sulfite [7] | | 0.5 | 0.5 | 0.5 | 0.5 | 0.5 | 0.5 | 0.5 | 0.5 |
| Carboxy vinyl polymer [8] | | 0.5 | 0.5 | 0.5 | 0.5 | 0.5 | 0.5 | 0.5 | 0.5 |
| Monoethanolamine [9] | | 8.0 | 3.0 | Moderate | 3.0 | 3.0 | 8.0 | 3.0 | 3.0 |
| Phosphoric acid (75%) [10] | | 0.4 | 0.4 | — | 0.4 | 0.4 | 0.4 | 0.4 | 0.4 |
| Water | | Remainder | Remainder | Remainder | Remainder | Remainder | Remainder | Remainder | Remainder |
| Sum total | % by mass | 100 | 100 | 100 | 100 | 100 | 100 | 100 | 100 |
| pH | | 10 | 10 | 7 | 10 | 10 | 10 | 10 | 10 |

The components described in Table 1 are shown below. All of the blending amounts (% by mass) described in Table 1 are tangible.

1) (A1): Solution produced by the method described in Japanese Patent No. 5570161 (5,6-dihydroxyindole: 1% by mass, 5,6-dihydroxyindole-2-carboxylic acid: 0.14% by mass, ethanol: 20% by mass, water: remainder)

2) (A2): 5,6-Dihydroxyindole solution (manufactured by Matrix Scientific Inc., 5,6-dihydroxyindole: 1% by mass, ethanol: 20% by mass, water: remainder)

3) (A3): 5,6-Dihydroxyindoline hydrobromide solution (manufactured by AK Scientific, Inc., 5,6-dihydroxyindoline hydrobromide: 1% by mass, ethanol: 20% by mass, water: remainder)

4) Oxidation dye X: Toluene-2,5-diamine sulfate, paraaminophenol, metaaminophenol, resorcin, 2,4-diaminophenoxyethanol hydrochloride, 5-aminoorthocresol, and paraphenylenediamine sulfate, each being 0.005% by mass (amount relative to the whole amount of the composition)

5) Oxidation dye Y: 2-Methylresorcin, 4-aminometacresol, 2-amino-3-hydroxypyridine, 2-amino-4-(6-hydroxyethyl)aminoanisole sulfate, 4-chlororesorcinol, 1-naphthol, and 1-hydroxyethyl-4,5-diaminopyrazole sulfate, each being 0.005% by mass (amount relative to the whole amount of the composition)

6) Ascorbic acid: L-Ascorbic acid crystal (manufactured from DSM Nutritional Products (UK) Ltd.)

7) Sodium sulfite: Purified anhydrous sodium sulfite (manufactured by Daito Chemical Co., Ltd.)

8) Carboxyvinyl polymer: CARBOPOL 981 POLYMER (manufactured by Lubrizol Advanced Materials, Inc.)

9) Monoethanolamine (manufactured by Mitsui Chemicals, Inc.)

10) Phosphoric acid: Food additive 75% phosphoric acid (manufactured by Nippon Chemical Industrial Co., Ltd., 75% by mass phosphoric acid aqueous solution)

Examples 1 to 12 and Comparative Examples 1 to 3 (Hair Treatment and Evaluation)

[Hair Bundle for Evaluation]

A curly hair of a Caucasian with no history of any chemical treatment was applied lightly with a load to stretch in a straight shape, thereby preparing a hair bundle having a length of 30 cm and a mass of 0.5 g. This hair bundle was cleansed with a shampoo having the following formulation and rinsed away, excessive water was then mopped up with a towel, and the resulting hair bundle was naturally dried under a laboratory condition for 12 hours and used for the evaluation.

| <Shampoo Formulation> | (% by mass) |
|---|---|
| Sodium polyoxyethylene lauryl ether sulfate (EMAL E-27C (active component amount: 27% by mass), manufactured by Kao Corporation) | 57.4 |
| Lauramide DEA (AMINON L-02, manufactured by Kao Corporation) | 1.5 |
| EDTA-2Na (FROST DS, manufactured by Daiichi Pure Chemical Co., Ltd.) | 0.3 |
| Phosphoric acid (adjusted at a pH of 7.0) | Moderate |
| Purified water | Remainder |
| Total | 100 |

[Hair Treatment Method]

Examples 1 to 10 and Comparative Examples 1 to 2

0.5 g of each of compositions shown in Table 2 was applied on the dried hair bundle for evaluation (step (i); however, step (i)' in Comparative Example 1) and uniformly made familiar with the hair for 1 minute, and the resulting hair bundle in a state where the composition was applied was allowed to stand at 30° C. for 5 minutes. Subsequently, the hair bundle was rinsed away with tap water at 40° C. for 30 seconds and then dried with a towel, followed by naturally drying at room temperature for 6 hours.

Thereafter, the vicinity of the root of the hair bundle was held with a flat-type hair iron set to a temperature shown in Table 2, and an operation of sliding at a speed of 6 cm/sec while stretching from the root of the hair toward the hair end direction was performed three times, thereby carrying out the step (ii) (step (ii)' in Comparative Example 2). As the flat-type hair iron, "CIS-W28N", manufactured by Create Ion Co., Ltd. was used under a heating condition at 200° C. or lower, and "WPS-01", manufactured by Osaka Brush Co., Ltd. was used under a heating condition at higher than 200° C.

Example 11

The step (i) was performed by using the composition A, and the same operation as in Example 1 was performed until rinsing away the composition. Subsequently, the hair was treated by the same operation as in Example 1, except that 1 g of a shampoo having the aforementioned formulation was applied and lathered for 30 seconds, and the rinsing step was then performed for 30 seconds, followed by carrying out the step (ii).

Example 12

The hair was treated by the same operation as in Example 1, except that the step (i) was performed by using the composition A, the foregoing composition was made familiar with the hair for 1 minute and immediately thereafter, rinsed away with tap water at 40° C. for 30 seconds.

Comparative Example 3

The dried hair bundle for evaluation was subjected to the same operation as in the step (i) of Example 1 by using a flat-type hair iron set at 200° C. ("CIS-W28N", manufactured by Create Ion Co., Ltd.). Subsequently, 0.5 g of the composition A was applied on this hair bundle (step (i)) and uniformly made familiar with the hair for 1 minute, and the resulting hair bundle in a state where the composition was applied was allowed to stand at 30° C. for 5 minutes. Subsequently, the hair bundle was rinsed away with tap water at 40° C. for 30 seconds and then dried with a towel, followed by naturally drying at room temperature for 6 hours.

[Evaluation of Resistance to Shampooing]

On the occasion of lightly applying a load on an untreated hair bundle for evaluation to stretch in a straight shape, a length of the hair bundle was defined as L (cm). After cleansing an untreated hair bundle for evaluation and then naturally drying, a length of the longest portion thereof was defined as $L_0$ (cm), and in each of the Examples, a length of the longest portion of the hair bundle after performing the aforementioned hair treatment was defined as $L_1$ (cm).

Subsequently, the hair bundle (length: $L_1$) after the aforementioned treatment, as obtained in each of the Examples, was wetted with tap water at 40° C. for 30 seconds, and 1 g of the shampoo having the aforementioned formulation was applied on the hair bundle and lathered for 30 seconds, followed by rinsing away for 30 seconds, to achieve shampooing. Subsequently, after drying with a towel, the resulting hair bundle was naturally dried at room temperature for 12 hours. A length of the longest portion of this hair bundle after natural drying was defined as $L_2$ (cm), and a shape keeping rate (%) after shampooing was determined according to the following expression. $L_0$, $L_1$, and $L_2$ are each a length obtained by hanging down the hair bundle from above and performing the measurement without being drawn. The results are shown in Table 2.

Shape keeping rate (%) after shampooing=$(L_2-L_0)/(L_1-L_0)\times 100$

TABLE 2

| | Example | | | | | | | | |
|---|---|---|---|---|---|---|---|---|---|
| | 1 | 2 | 3 | 4 | 5 | 6 | 7 | 8 | 9 |
| Composition | A | E | F | A | A | A | C | D | G |
| Hair treatment method | Step (i) Allowed to stand for 5 minutes Rinsing Drying Step (ii) at 200° C. | Step (i) Allowed to stand for 5 minutes Rinsing Drying Step (ii) at 200° C. | Step (i) Allowed to stand for 5 minutes Rinsing Drying Step (ii) at 200° C. | Step (i) Allowed to stand for 5 minutes Rinsing Drying Step (ii) at 220° C. | Step (i) Allowed to stand for 5 minutes Rinsing Drying Step (ii) at 180° C. | Step (i) Allowed to stand for 5 minutes Rinsing Drying Step (ii) at 140° C. | Step (i) Allowed to stand for 5 minutes Rinsing Drying Step (ii) at 200° C. | Step (i) Allowed to stand for 5 minutes Rinsing Drying Step (ii) at 200° C. | Step (i) Allowed to stand for 5 minutes Rinsing Drying Step (ii) at 200° C. |
| Shape keeping rate after shampooing [1] | 50.0% | 57.1% | 16.7% | 51.1% | 25.0% | 20.0% | 42.9% | 42.9% | 16.7% |
| L (cm) | 30.0 | 30.0 | 30.0 | 30.0 | 30.0 | 30.0 | 30.0 | 30.0 | 30.0 |
| $L_0$ (cm) | 26.0 | 26.5 | 27.0 | 25.5 | 26.0 | 26.0 | 26.5 | 26.5 | 27.0 |
| $L_1$ (cm) | 30.0 | 30.0 | 30.0 | 30.0 | 30.0 | 28.5 | 30.0 | 30.0 | 30.0 |
| $L_2$ (cm) | 28.0 | 28.5 | 27.5 | 27.8 | 27.0 | 26.5 | 28.0 | 28.0 | 27.5 |

| | Example | | | Comparative Example | | |
|---|---|---|---|---|---|---|
| | 10 | 11 | 12 | 1 | 2 | 3 |
| Composition | H | A | A | B | A | A |
| Hair treatment method | Step (i) Allowed to stand for 5 minutes Rinsing Drying Step (ii) at 200° C. | Step (i) Allowed to stand for 5 minutes Rinsing Drying Step (ii) at 200° C. | Step (i) Allowed to stand for 5 minutes Rinsing Shampooing Rinsing Drying Step (ii) at 200° C. | Step (i) Rinsing Drying Step (ii) at 200° C. | Step (i) Allowed to stand for 5 minutes Rinsing Drying Step (ii)' at 130° C. | Step (ii) at 200° C. Step (i) Allowed to stand for 5 minutes Rinsing Drying — |

TABLE 2-continued

|  | | | | | | |
|---|---|---|---|---|---|---|
| Shape keeping rate after shampooing [1] | 20.0% | 50.0% | 30.0% | 0.0% | 0.0% | 0.0% |
| L (cm) | 30.0 | 30.0 | 30.0 | 30.0 | 30.0 | 30.0 |
| $L_0$ (cm) | 27.5 | 26.0 | 25.0 | 25.5 | 26.5 | 25.0 |
| $L_1$ (cm) | 30.0 | 30.0 | 30.0 | 30.0 | 28.0 | 26.0 |
| $L_2$ (cm) | 28.0 | 28.0 | 26.5 | 25.5 | 26.5 | 25.0 |

[1] Shape keeping rate (%) after shampooing: $(L_2 - L_0)/(L_1 - L_0) \times 100$
L (cm): Length of the untreated hair bundle having been drawn and stretched
$L_0$ (cm): Length after cleansing the untreated hair bundle, followed by naturally drying
$L_1$ (cm): Length after naturally drying the hair bundle after treatment
$L_2$ (cm): Length after cleansing the hair bundle after treatment, followed by naturally drying The following are noted from Tables 1 and 2.

In Examples 1 to 12 in which the hair treatment was performed by using the composition containing the component (A) through the step (i) and the step (ii) in this order, even by shampooing after the treatment, the shape given to the hair in the step (ii) can be kept to some extent.

In contrast, in all of Comparative Example 1 in which the heat treatment was performed by using the composition B not containing the component (A) in the step (i), Comparative Example 2 in which the shape was given at a temperature of lower than 140° C. in the step (ii), and Comparative Example 3 in which the step (i) and the step (ii) were not performed in this order, but the step (ii) was performed in advance, the shape of the hair after shampooing returned to the original state, and the shape could not be kept.

INDUSTRIAL APPLICABILITY

In accordance with the hair treatment method of the present invention, it is possible to give a shape to the hair without chemically denaturing a hair protein and to keep the shape even after shampooing. In addition, in accordance with the hair treatment method of the present invention, since the composition containing a predetermined melanin precursor is used, it is also possible to form a melanin dye in the hair owing to oxidation polymerization of the melanin precursor, to achieve hair dyeing.

The invention claimed is:

1. A method for treating hair, comprising (i) and (ii) in this order:
   (i) applying a composition comprising from 0.02% by mass to 5% by mass of 5,6-dihydroxyindole or a salt thereof;
   (ii) giving a shape to the hair while applying a temperature of from 140° C. to 220° C. to the hair,
   wherein a pH of the composition is from 8.0 to 12.0, and
   wherein the method does not comprise applying to the hair a hair treatment agent comprising a reducing agent or a hair treatment agent having a pH of more than 12.

2. The method according to claim 1, wherein the composition further comprises an antioxidant.

3. The method according to claim 1, further comprising, between (i) and (ii), allowing the hair on which the composition is applied to stand for at least 1 minute.

4. The method according to claim 1, further comprising, between (i) and (ii), rinsing the hair.

5. The method according to claim 1, wherein (ii) comprises applying the temperature of from 140° C. to 220° C. from the root of the wavy hair toward the hair end direction, thereby giving a relaxed shape to the hair.

6. The method according to claim 1, wherein (ii) is performed by using a hair iron.

7. The method according to claim 1, wherein an amount of the composition applied on the hair in (i) is from 0.05 to 1.5 in terms of a bath ratio to the mass of hair [(mass of composition)/(mass of hair)].

8. The method according to claim 1, wherein the composition is a hair cleansing agent, a hair rinse, a hair conditioning agent, a hair styling agent, a hair dye, or a hair growth promoter.

9. The method according to claim 2, wherein the antioxidant is at least one compound selected from the group consisting of sulfurous acid, ascorbic acid, L-cysteine, and N-acetyl-L-cysteine, and a salt thereof.

10. The method according to claim 2, wherein the antioxidant is at least one compound selected from the group consisting of ascorbic acid and a salt thereof.

11. The method according to claim 1, wherein a dyeing agent other than component (A) in the composition is 0.03% by mass or less.

* * * * *